United States Patent [19]
Dershem et al.

[11] Patent Number: 6,034,194
[45] Date of Patent: Mar. 7, 2000

US006034194A

[54] BISMALEIMIDE-DIVINYL ADHESIVE COMPOSITIONS AND USES THEREFOR

[75] Inventors: Stephen M. Dershem, San Diego; Dennis B. Patterson, La Jolla; Jose A. Osuna, Jr., San Diego, all of Calif.

[73] Assignee: Quantum Materials/Dexter Corporation, San Diego, Calif.

[21] Appl. No.: 08/300,721

[22] Filed: Sep. 2, 1994

[51] Int. Cl.$^7$ .................................................. C08F 222/40
[52] U.S. Cl. ............................................. 526/262; 524/548
[58] Field of Search ............................... 526/262; 524/548

[56] References Cited

U.S. PATENT DOCUMENTS

| | | | |
|---|---|---|---|
| 4,193,829 | 3/1980 | Kourtides et al. . | |
| 4,578,328 | 3/1986 | Kray . | |
| 4,581,461 | 4/1986 | Rossi et al. | 548/406 |
| 4,621,122 | 11/1986 | Guilbert et al. . | |
| 4,740,830 | 4/1988 | Ketley . | |
| 4,743,642 | 5/1988 | Yanacek et al. . | |
| 4,803,250 | 2/1989 | Nagasaki et al. . | |
| 4,806,608 | 2/1989 | Klemarczyk | 526/262 |
| 4,853,449 | 8/1989 | Domeier | 526/259 |
| 4,904,360 | 2/1990 | Wilson, Jr. et al. . | |
| 5,153,248 | 10/1992 | Muse et al. . | |
| 5,246,784 | 9/1993 | Fuchs et al. . | |
| 5,328,636 | 7/1994 | Maly et al. . | |
| 5,364,700 | 11/1994 | Domeier . | |
| 5,380,768 | 1/1995 | Carnston et al. | 521/167 |
| 5,475,048 | 12/1995 | Jamison et al. | 524/439 |

FOREIGN PATENT DOCUMENTS

| | | | |
|---|---|---|---|
| 93/25386 | 12/1993 | WIPO | B32B 19/00 |

*Primary Examiner*—Bernard Lipman
*Attorney, Agent, or Firm*—Gray Cary Ware & Freidenrich; Stephen E. Reiter; Ramsey R. Stewart

[57] ABSTRACT

In accordance with the present invention, there are provided novel adhesive compositions which do not require solvent to provide a system having suitable viscosity for convenient handling and cure rapidly. The resulting thermosets are stable to elevated temperatures, are highly flexible, have low moisture uptake and good adhesion to both the substrate and the device attached thereto.

13 Claims, No Drawings

BISMALEIMIDE-DIVINYL ADHESIVE COMPOSITIONS AND USES THEREFOR

The present invention relates to adhesive compositions and uses therefor. In a particular aspect, the present invention relates to die attach compositions useful for attaching semiconductor devices to carrier substrates.

BACKGROUND OF THE INVENTION

Bismaleimides per se occupy a prominent position in the spectrum of thermoset resins. Indeed, several bismaleimides are commercially available. The co-cure of simple bismaleimides with relatively simple divinyl ethers is also known in the art. However, neither simple bismaleimides nor bismaleimide/divinyl ether systems are believed to have received application in the area of die attach adhesives. In this context, several criteria are believed to be critical to successful commercial application:

1. The adhesive composition should have good handling properties, without the need to add solvent thereto (i.e., a 100% reactive liquid monomer system of sufficiently low viscosity);
2. The adhesive composition should be capable of rapid ("snap") cure, i.e., two minutes or less at $\leq 200°$ C.;
3. The resulting thermoset should be stable to at least 250° C., wherein "stable" is defined as less than 1% weight loss at 250° C. when subjected to a temperature ramp of 10° C./min. in air via thermogravimetric analysis (TGA);
4. The resulting thermoset should be sufficiently flexible (radius of curvature >1.0 meter) to allow use in a variety of high stress applications;
5. The resulting thermoset should exhibit low-moisture uptake (to be used in nonhermetic packages); and
6. The resulting thermoset should exhibit good adhesion to substrate, even after strenuous exposure to moisture.

With respect to the requirement for low moisture uptake by the thermoset, for example, relatively high moisture uptake is a known drawback of prior art bismaleimide thermosets. In addition, prior art systems have not provided the combination of properties desired for the applications contemplated herein.

BRIEF DESCRIPTION OF THE INVENTION

In accordance with the present invention, we have developed novel adhesive compositions which meet all of the above criteria, i.e., do not require solvent to provide a system of suitable viscosity for convenient handling and rapidly cure. The resulting thermosets are stable to elevated temperatures, are highly flexible, have low moisture uptake and good adhesion to both the substrate and device attached thereto.

DETAILED DESCRIPTION OF THE INVENTION

In accordance with the present invention, there are provided adhesive compositions comprising:

(a) a bismaleimide of defined structure,
(b) up to one equivalent of a divinyl compound of defined structure per equivalent of bismaleimide,
(c) in the range of 0.1 up to 10 wt % of at least one coupling agent, based on the total weight of the composition, and
(d) in the range of 0.2 up to 3 wt % of at least one free radical initiator, based on the total weight of organic materials in the composition, i.e., in the absence of filler.

Bismaleimides contemplated for use in the practice of the present invention are compounds having the structure:

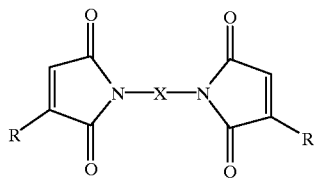

where in:
each R is independently selected from hydrogen or lower alkyl, and
—X— is selected from:
saturated straight chain alkylene or branched chain alkylene, optionally containing saturated cyclic moieties as substituents on said alkylene chain or as part of the backbone of the alkylene chain, wherein said alkylene species have at least 6 carbon atoms,
aromatic bridging groups having the structure:

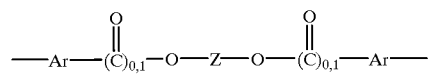

wherein each Ar is a disubstitutecl or trisubstituted aromatic or heteroaromatic ring having in the range of 3 up to 10 carbon atoms, and Z is selected from:
saturated straight chain alkylene or branched chain alkylene, optionally containing saturated cyclic moieties as substituents on said alkylene chain or as part of the backbone of the alkylene chain, wherein said alkylene species have at least 6 carbon atoms,
siloxanes having the structure:

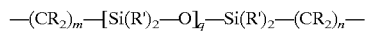

wherein each R is independently defined as above, and each R' is independently selected from hydrogen, lower alkyl or aryl, m falls in the range of 1 up to 10, n falls in the range of 1 up to 10, and q falls in the range of 1 up to 50,
polyalkylene oxides having the structure:

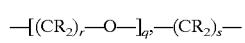

wherein each R is independently as defined above, r falls in the range of 1 up to 10, s falls in the range of 1 up to 10, and q' falls in the range of 1 up to 50,
di- or tri-substituted aromatic moieties having the structure:

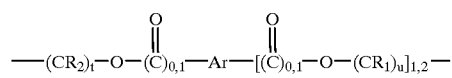

wherein each R is independently as defined above, t falls in the range of 2 up to 10, u falls in the range of 2 up to 10, and Ar is as defined above,
siloxanes having the structure:

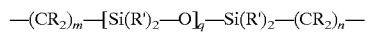

wherein each R and R' is independently defined as above, and wherein each of m, n and q are as defined above, polyalkylene oxides having the structure:

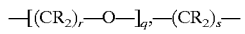

wherein each R is independently as defined above, and wherein each of r, s and q' are as defined above, as well as mixtures of any two or more thereof.

Exemplary bismaleimides embraced by the above generic structure include bismaleimides prepared by reaction of maleic anhydride with dimer amines (i.e., α,ω-diamino hydrocarbons prepared from dimer acids, a mixture of mono-, di- and tri-functional oligomeric, aliphatic carboxylic acids; dimer acids are typically prepared by thermal reaction of unsaturated fatty acids, such as oleic acid, linoleic acid, and the like, which induces Diels-Alder and ene reactions leading to the above-mentioned mixture of components). An exemplary bismaleimide which can be prepared from such dimer amines is 1,20-bismaleimido-10,11-dioctyl-eicosane, which would likely exist in admixture with other isomeric species produced in the ene/Diels-Alder reactions employed to produce dimer acids. Other bismaleimides contemplated for use in the practice of the present invention include BMIs prepared from α,ω-aminopropyl-terminated polydimethyl siloxanes (such as "PS510" sold by Huls America, Piscataway, N.J.), polyoxypropylene amines (such as "D-230", "D-400", "D-2000" and "T-403", sold by Texaco Chemical Company, Houston, Tex.), polytetramethyleneoxide-di-p-aminobenzoates (such as the family of such products sold by Air Products, Allentown, Pa., under the tradename "Versalink" e.g., "Versalink P-650"), and the like.

Bismaleimides can be prepared employing techniques well known to those of skill in the art. The most straightforward preparation of maleimides entails formation of the maleamic acid via reaction of the corresponding primary amine with maleic anhydride, followed by dehydrative closure of the maleamic acid with acetic anhydride. A major complication is that some or all of the closure is not to the maleimide, but to the isomaleimide. Essentially the isomaleimide is the dominant or even exclusive kinetic product, whereas the desired maleimide is the thermodynamic product. Conversion of the isomaleimide to the maleimide is effectively the slow step and, particularly in the case of aliphatic amines, may require forcing conditions which can lower the yield. Nevertheless, in the case of a stable backbone such as that provided by a long, branched chain hydrocarbon (e.g., —(CH$_2$)$_9$—CH(C$_8$H$_{17}$)—CH(C$_8$H$_{17}$)—(CH$_2$)$_9$—), the simple acetic anhydride approach appears to be the method of choice. Of course, a variety of other approaches can also be employed.

For example, dicyclohexylcarbodiimide (DCC) closes maleamic acids much more readily than does acetic anhydride. With DCC, the product is exclusively isomaleimide. However, in the presence of suitable isomerizing agents, such as 1-hydroxybenzotriazole (HOBt), the product is solely the maleimide. The function of the HOBt could be to allow the closure to proceed via the HOBt ester of the maleamic acid (formed via the agency of DCC) which presumably closes preferentially to the maleimide. However, it is unclear why such an ester should exhibit such a preference. In any case, it is demonstrated herein that isomide generated by reaction of the bismaleamic acid of 10,11-dioctyleicosane with either acetic acid anhydride or EEDQ (2-ethoxy-1-ethoxycarbonyl-1,2-dihydroquinoline) is isomerized to the bismaleimide by catalytic amounts of HOBt. 3-Hydroxy-1,2,3-benzotriazine-4-one appears to be at least as effective as HOBt in effecting this isomerization, whereas N-hydroxysuccinimide is substantially less so.

Likely, isomerizing agents such as HOBt add to the isoimide to yield the amic acid ester. If this exhibits any tendency whatsoever to close to the imide, much less a strong bias for doing so, a route for interconverting isoimide and imide is thereby established and the thermodynamic product, imide, should ultimately prevail. Thus if the initial closure of ester formed in the DCC reaction yields any isoimide, or if any isoimide is produced by direct closure of the acid, the situation will be subsequently "corrected" via conversion of the isoimide to the imide by the action of the active ester alcohol as an isomerizing agent.

One problem encountered with bismaleimides is a proclivity for oligomerization. This oligomerization is the principle impediment to yield in the synthesis of bismaleimides, and may present problems in use. Radical inhibitors can mitigate this potential problem somewhat during the synthesis but these may be problematic in use. Fortunately, oligomer may be removed by extracting the product into pentane, hexane or petroleum ether, in which the oligomers are essentially insoluble.

Divinyl compounds contemplated for use in the practice of the present invention are compounds having the structure:

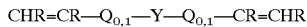

wherein:
each R is independently as defined above,
each Q is independently selected from —O—, —O—C(O)—, —C(O)— or —C(O)—O—, and
—Y— is selected from:
saturated straight chain alkylene or branched chain alkylene, optionally containing saturated cyclic moieties as substituents on said alkylene chain or as part of the backbone of the alkylene chain, wherein said alkylene species have at least 6 carbon atoms,
di- or tri-substituted aromatic moieties having the structure:

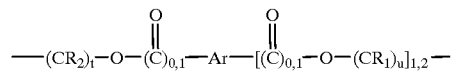

wherein each R is independently as defined above, Ar is as defined above, and each of t and u are as defined above,
polysiloxanes having the structure:

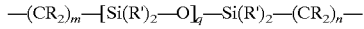

wherein each R and R' is independently defined as above, and wherein each of m, n and q are as defined above,
polyalkylene oxides having the structure:

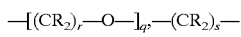

wherein each R is independently as defined above, and wherein each of r, s and q' are as defined above, as well as mixtures of any two or more thereof.

Exemplary divinyl compounds embraced by the above generic structure include tetraethylene glycol divinyl ether, 4,4'-divinyl (isopropylidenedicyclohexyl) ether, tris-2,4,6-(1-vinyloxybutane-4-)oxy-1,3,5-triazine, bis-1,3-(1-vinyloxybutane-4-)oxycarbonyl-benzene (alternately referred to as bis(4-vinyloxybutyl)isophthalate; available from Allied-Signal Inc., Morristown, N.J., under the tradename Vectomer™ 4010), divinyl ethers prepared by trans-vinylation between lower vinyl ethers and higher molecular weight di-alcohols (e.g., α, ω-dihydroxy hydrocarbons prepared from dimer acids, as described above; an exemplary divinyl ether which can be prepared from such dimer alcohols is 10,11-dioctyl eicosane-1,20-divinyl ether, which would likely exist in admixture with other isomeric species produced in the ene/Diels-Alder reactions employed to produce dimer acids), in the presence of a suitable palladium catalyst (see, for example, Example 9), and the like.

In preferred embodiments of the present invention, either —X— (of the bismaleimide) or —Y— (of the divinyl compound) can be aromatic, but both —X— and —Y— are not aromatic in the same formulation.

As employed herein, the term "coupling agent" refers to chemical species that are capable of bonding to a mineral surface and which also contain polymerizably reactive functional group(s) so as to enable interaction with the adhesive composition. Coupling agents thus facilitate linkage of the adhesive composition to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). Generally in the range of about 0.1 up to 10 wt % of at least one coupling agent (based on the total weight of the organic phase) will be employed, with in the range of about 0.5 up to 2 wt % preferred.

Presently preferred coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention adhesive composition. Especially preferred coupling agents contemplated for use in the practice of the invention are oligomeric silicate coupling agents such as poly (methoxyvinylsiloxane).

In addition to the incorporation of coupling agents into invention adhesive compositions, it has also been found that the optional incorporation of a few per cent of the precursor bismaleamic acid greatly increases adhesion. Indeed, good adhesion is retained even after strenuous exposure to water.

As employed herein, the term "free radical initiator" refers to any chemical species which, upon exposure to sufficient energy (e.g., light, heat, or the like), decomposes into two parts which are uncharged, but which each possess at least one unpaired electron. Preferred as free radical initiators for use in the practice of the present invention are compounds which decompose (i.e., have a half life in the range of about 10 hours) at temperatures in the range of about 70 up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis (cyclohexanecarbonitrile)), and the like. Peroxide initiators are presently preferred because they entail no gas release upon decomposition into free radicals. Those of skill in the art recognize, however, that in certain adhesive applications, the release of gas (e.g. $N_2$) during cure of the adhesive would be of no real concern. Generally in the range of about 0.2 up to 3 wt % of at least one free radical initiator (based on the total weight of the organic phase) will be employed, with in the range of about 0.5 up to 1.5 wt % preferred.

In accordance with another embodiment of the present invention, there are provided die-attach pastes comprising:

in the range of about 10 up to 80 wt % of the above-described adhesive composition, and in the range of about 20 up to 90 wt % filler.

Fillers contemplated for use in the practice of the present invention can be electrically conductive and/or thermally conductive, and/or fillers which act primarily to modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds which act primarily to modify rheology include fumed silica, alumina, titania, and the like.

In accordance with yet another embodiment of the present invention, there are provided assemblies of components adhered together employing the above-described adhesive compositions and/or die attach compositions. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like.

Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

In accordance with still another embodiment of the present invention, there are provided methods for adhesively attaching two component parts to produce the above-described assemblies. Thus, for example, a first article can be adhesively attached to a second article, employing a method comprising:

(a) applying the above-described adhesive composition to said first article, (b) bringing said first and second article into intimate contact to form an assembly wherein said first article and said second article are separated only by the adhesive composition applied in step (a), and thereafter, (c) subjecting said assembly to conditions suitable to cure said adhesive composition.

Similarly, a microelectronic device can be adhesively attached to a substrate, employing a method comprising:

(a) applying the above-described die attach paste to said substrate and/or said microelectronic device, (b) bringing said substrate and said device into intimate contact to form an assembly wherein said substrate and said device are separated only by the die attach composition applied in step (a), and thereafter, (c) subjecting said assembly to conditions suitable to cure said die attach composition.

Conditions suitable to cure invention die attach compositions comprise subjecting the above-described assembly to a temperature of less than about 200° C. for about 0.5 up to 2 minutes. This rapid, short duration heating can be accomplished in a variety of ways, e.g., with an in-line heated rail, a belt furnace, or the like.

In accordance with a still further embodiment of the present invention, there is provided a method for the preparation of bismaleimides from diamines. The invention synthetic method comprises:

adding diamine to a solution of maleic anhydride, adding acetic anhydride to said solution once diamine addition is complete, and then allowing the resulting mixture to stir overnight, and thereafter treating the resulting reaction mixture with a suitable isomerizing agent.

Diamines contemplated for use in the practice of the present invention include saturated and unsaturated dimer diamines (such as the dimer amines sold by Henkel Corporation, Ambler, Pa, under the tradename "Versamine 552" and "Versamine 551"), α,ω-aminopropyl-terminated polydimethyl siloxanes (such as "PS510" sold by Hüls America, Piscataway, N.J.), polyoxypropylene amines (such as "D-230", "D-400", "D-2000" and "T-403", sold by Texaco Chemical Company, Houston, Tex.), polytetramethyleneoxide-di-p-aminobenzoate (such as the family of such products sold by Air Products, Allentown, Pa, under the tradename "Versalink" e.g., "Versalink P-650"), and the like. Diamine and maleic anhydride are typically combined in approximately equimolar amounts, with a slight excess of maleic anhydride preferred. Isomerizing agents contemplated for use in the practice of the present invention include 1-hydroxybenzotriazole, 3-hydroxy-1,2,3-benzotriazine-4-one, 1-hydroxy-7-azabenzotriazole, N-hydroxysuccinimide, and the like.

The invention will now be described in greater detail by reference to the following non-limiting examples.

EXAMPLE 1

Preparation of the bismaleimide of hydrogenated dimer acid diamine (Henkel Corp. Versamine 552) by closure of the bismaleamic acid with acetic anhydride to a mixture of isomaleimide and maleimide, followed by isomerization of the isomaleimide to maleimide with 1-hydroxybenzotriazole (HOBt) under mild conditions. A solution of 30.0 g of Versamine 552 in 90 mL of anhydrous tetrahydrofuran (THF) was slowly added to a solution of 12.5 g of maleic anhydride in 60 mL of THF. One hour after completion of the addition, 125 mL of acetic anhydride was added and the reaction mixture stirred overnight under argon atmosphere.

A Fourier transform infrared attenuated total reflectance (FTIR ATR) spectrum indicated substantial conversion of the amic acid to the isoimide, with little if any amide. The reaction mixture was brought to reflux and maintained there for three hours. FTIR now indicated a mixture of isoimide and maleimide with the former apparently (uncalibrated spectrum) predominating. Benzoquinone, 0.1 g, was added to the reaction mixture and the solvent/acetic anhydride/acetic acid stripped under vacuum (ultimately 0.1 mm Hg) at 30° C. The resulting residue was taken up in 75 mL of fresh THF and 10.2 g of HOBt (<5% H$_2$O material) was added and dissolved in at room temperature.

An FTIR spectrum one hour after the addition indicated that the isomaleimide in the mixture had been largely, perhaps completely, consumed. Most of it appeared to have been converted to maleamic acid HOBt ester. The reaction mixture was stirred overnight. FTIR then indicated essentially complete conversion to the maleimide.

The solvent was stripped off at 30° C. and the residue extracted 2× with several hundred mL of pentane. The combined pentane fractions were chilled in a Dry Ice/ isopropyl alcohol bath, which caused a white solid to crystallize out. (The solid is thought to be the acetate of HOBt, with some free HOBt). The pentane suspension was filtered cold, allowed to warm to room temperature, dried over anhydrous MgSO$_4$ and the solvent stripped to give 16.9 g (43.8%) of high purity product (as determined by FTIR).

EXAMPLE 2

Bismaleamic acid was generated from 10.0 g of Versamine 552 and 3.9 g of maleic anhydride, each in 40 mL of THF. 2-Ethoxy-1-ethoxycarbonyl-1,2-dihydroquinoline (EEDQ), 9.3 g, was added. Monitoring by FTIR indicated that two days sufficed to effect essentially complete conversion to isomaleimide. HOBt, 4.9 g, was dissolved in the reaction mixture. Monitoring by FTIR indicated that six hours sufficed to convert all the isoimide to imide. The solvent was stripped off and the residue extracted with pentane to yield 6.0 g of product bismaleimide, contaminated with quinoline from the EEDQ.

EXAMPLE 3

E. C. Martin and A. A. DeFusco, in U.S. Statutory Invention Registration H424 (Feb. 2, 1988) teach the preparation of bismaleimide from "dimer diamine" (source not given but material NOT having had the olefinic unsaturated removed) by means of HOBt and DCC. However, the maximum yield of bismaleimide reported is 50%. Thus, following the procedure of Martin and Fusco, the bismaleimide of Versamine 552 (Henkel Corp.) was prepared using dicyclohexylcarbodiimide (DCC) and 1-hydroxybenzotriazole (HOBt). A solution of 50.0 g (0.179 amine equiv) of Versamine 552 in 60 mL of anhydrous tetrahydrofuran (THF) was added slowly under argon atmosphere to a solution of 20.2 g (0.206 mole) of maleic anhydride in 300 mL of THF. The reaction mixture was stirred for an hour after completion of the addition and then 25.2 g (0.186 mole) of HOBt (<5% H$_2$O) was dissolved in. The stirred reaction mixture was chilled in an ice bath and melted DCC added neat in portions to a total of 49.2 g (0.238 mole). After completion of this addition, the reaction mixture was stirred in the ice bath for another hour. The ice bath was then removed and the stirred reaction mixture allowed to warm to room temperature overnight. The reaction mixture was filtered and the resulting solid was washed with THF. All THF phases were combined, 0.2 g methoxyphenol was added and the THF stripped on a rotary evaporator at 30° C. A thick, semisolid residue resulted. This residue was extracted with hexane and the hexane stripped to give 40.7 g (63.3%) of a product which still had some solid impurity. This material was extracted with pentane, which cleanly separated the solid impurity. The pentane extract was dried over MgSO$_4$ and the solvent stripped to give 32.1 g (49.9%) of lightly colored, low viscosity material with the expected FTIR spectrum.

EXAMPLE 4

This example illustrates improvement in yield obtained by using 3-hydroxy-1,2,3-benzotriazin-4-one (HOBtCO) instead of HOBt. The bismaleamic acid of Versamine 552 was prepared by the dropwise addition over an hour (dry argon atmosphere) of a solution of 144.0 g of Versamine 552 in 100 mL of dry dichloromethane ($CH_2Cl_2$) to a stirred solution of 50.4 g maleic anhydride in 300 mL of dry $CH_2Cl_2$ chilled in an ice bath. The ice bath was removed at the end of the addition and the reaction mixture stirred for another hour. The ice bath was then put back in place and 84.0 g (100%) of 3-hydroxy-1,2,3-benzotriazin-4-one was added. To the chilled reaction mixture was then added a solution of 106.1 g of DCC in 100 mL of $CH_2Cl_2$ over 30 minutes, with stirring. After completion of the addition, the ice bath was removed and the reaction mixture stirred overnight at room temperature. The reaction mixture was suction-filtered and the collected solid was washed twice with 100 mL portions of $CH_2Cl_2$, which were combined with the original $CH_2Cl_2$ filtrate. The $CH_2Cl_2$ was stripped on a rotary evaporator, at 35–40° C., ultimately under oil-pump vacuum (0.1 Torr). The resulting residue was extracted twice with 500 mL portions of pentane and once with a 1000 mL portion of pentane, all of which were combined and stripped on the rotary evaporator. The original residue was extracted with more pentane for a final total of four liters of pentane. After condensation to a volume of 500 mL, the solution was stored in the freezer overnight. It was allowed to warm to room temperature, suction-filtered through fine filter paper and the remaining pentane stripped to yield 145.0 g (80.0%) of the bismaleimide.

EXAMPLE 5

This example demonstrates that a very satisfactory yield may be obtained using much less than an equivalent of the coreactant compound, HOBt6CO, and that it may be added after the DCC. The bismaleamic acid of Versamine 552 was generated as in Example 4 from 136.5 g of Versamine 552 and 46.3 g of maleic anhydride, except that the solvent was THF rather than $CH_2Cl_2$. To the chilled (ice bath) reaction mixture was added a THF solution of DCC containing 100.5 g of DCC. After an FTIR spectrum showed that the amic acid had been entirely converted to isoimide, 12 g (15%) of HOBtCO was added and the reaction mixture maintained at 45° C. for four hours, which sufficed, by FTIR, to convert the isoimide entirely to imide. Workup as in the preceding example resulted in a yield of 122 g (70%) of the bismaleimide.

EXAMPLE 6

This example illustrates the use of 1-hydroxy-7-aza-1,2,3-benzotriazole (HOAt) as the coreactant compound, again at a low level. Using the procedure described in the preceding example but with 20% HOAt, 51.5 g of Versamine 552 yielded 48.8 g (70.0%) of the BMI. Separation of the HOAt from the reaction product was facile and 4.4 g was recovered.

EXAMPLE 7

The following experiments demonstrate improvements in the yield, obtained by the procedure of Martin and Fusco by changes in procedure and protocol while still using HOBt. The procedure and protocol used is that detailed in Example 4 in which 3-hydroxy-1,2,3-benzotriazin-4-one is used except that the reaction solvent was THF in all cases here rather than the dichloromethane used in Example 4. A reaction using 100% HOBt gave a yield of 51.9%; four reactions using 80% HOBt gave yields of 56.8, 60.0, 65.1 and 70,2%, respectively. Also, a reaction employing dimer diamine in which the olefinic unsaturation has not been removed, as in H424 (Henkel versamine 551 rather than 552) and 80% HOBt gave a yield of 52.2% of the corresponding BMI.

Examples 4–7 show that by variations in solvent and procedures, yields as high as 70% may be obtained using HOBt and as high as 80% using 3-hydroxy-1,2,3-benzotriazin- 4-one (HOBtCO) in lieu of HOBt. Also the realization in the course of the present work that compounds such as HOBt and HOBtCO are potent agents for the isoimide to imide isomerization means that the reaction may be run with less than a full equivalent of such. The fact that such compounds are first consumed and then liberated during the cyclodehydration, and are thus in principle catalysts, does not of itself necessarily imply that they may be used at less than a full equivalent since the potentially competing reaction of direct cyclodehydration of the amic acid by DCC to the isoimide would still be of concern. However, as it turns out, HOBt, HOBtCO, and the like are effective at promoting the facile isomerization which leads to the desired product.

EXAMPLE 8

A masterbatch of the bisisomaleimide of Versamine 552 was prepared from 30.0 g of the amine, dissolved in 80 mL of anhydrous THF and added dropwise to a solution of 11.7 g of maleic anhydride in 100 mL of anhydrous THF to yield the bismaleamic acid, followed by the addition of 125 mL of neat acetic anhydride. One half of this reaction mixture was allowed to stand for three days at room temperature. The solvent and excess acetic anhydride were stripped to leave the isomaleimide. Portions of this isomaleimide were treated as follows. A 5.0 g sample was dissolved in anhydrous THF along with 2.6 g of 3-hydroxy-1,2,3-benzotraizin-4-one (HOBtCO). This solution was allowed to stand overnight, which sufficed to effect complete conversion to the maleimide, ultimately recovered in 56% yield. Another 5.0 g of the isomaleimide was treated with 2.3 g of HOBt in the same manner; a 46% yield of bismaleimide was recovered as well as a larger amount of oligomerized material than in the HBtCO reaction. A third portion of the isomaleimide, 4.9 g, was treated with 2.1 g of N-hydroxysuccinimide in acetonitrile solution. In this case, overnight reflux was used to effect conversion to the maleimide, recovered in only 36% yield.

EXAMPLE 9

A divinyl ether was prepared as follows from the dimer diol derived from oleic acid employing Pripol 2033 dimer diol obtained from Unichema North America (Chicago, Ill.), vinyl propyl ether obtained from BASF Corp. (Parsippany, N.J.), and palladium 1,10-phenanthroline diacetate [Pd (phen) $(OAc)_2$]. Thus, the Pripol was pre-dried over molecular sieves (3A) approximately 3 hours prior to use. Next, to a clean and dry 1 liter flask, with large oval Teflon stir bar, was added 149.1 grams (523.3 meqs) of Pripol 2033, 280 grams (3256 meqs) of vinyl propyl ether, and 1.0 grams Pd (phen) $(AcO)_2$ (2.5 meqs). The head space of the flask was purged with argon and the reaction flask fitted with an oil bubbler (to eliminate any pressure build up in the flask). The flask was placed on a magnetic stir plate and stirring initiated and continued for approximately 48 hours. The solution color changed from a light yellow to a deep dark brown. After 48 hours, an aliquot was removed and the bulk of the vinyl propyl ether was blown off using argon. An FTIR was performed on the residue and it was determined that virtually all the alcohol had reacted (i.e., no OH absorbance between 3400 and 3500 $cm^{-1}$ remained).

To the original solution approximately 10–15 grams of activated charcoal was added. The solution was mixed for approximately 1 hour on the magnetic stir plate, then about 5 grams of Celite was added. The activated charcoal and Celite were removed via suction filtration through a fritted funnel packed with additional Celite (about an additional 15 grams). The solution that passed through the funnel retained a slight brown color.

The bulk of the excess vinyl propyl ether was then removed using a rotary evaporator at a bath temperature of 35–40° C. under a partial (water aspirator) vacuum. Once condensation stopped, the cold traps were emptied and replaced. A full mechanical vacuum was then applied and continued at the 35–40° C. bath temperature for approximately 1 hour. The vacuum decreased to under 1.0 torr within an hour. Product recovered at this point was a light brown, low viscosity liquid.

The last traces of propyl vinyl ether were removed using a falling film molecular still (operated at a strip temperature of 70° C. and a vacuum of less than one torr). The product residence time in the still head was about 15 to 20 minutes and the complete stripping procedure required about two hours. The product, following this strip, had no residual odor characteristic of the vinyl propyl ether. Thermogravimetric analysis showed no significant weight loss by 200° C. The product, therefore, was considered to be free of the vinyl ether starting material and any propyl alcohol co-product.

EXAMPLE 10

An organic adhesive vehicle was prepared using 2.78 grams (1.0 equivalents) of the BMI prepared according to Example 8, 0.94 grams (0.5 equivalents) of the divinyl ether prepared according to Example 9, and 0.58 grams (0.5 equivalents) of Vectomer 4010 (i.e., bis(4-vinyloxybutyl) isophthalate). An additional 1% by weight dicumyl peroxide (initiator), 0.5% gamma-methacryloxypropyltrimethoxysilane (coupling agent), and 0.5% beta- (3,4-epoxycyclohexyl) ethyltrimethoxysilane (coupling agent) were added to complete the organic adhesive mix.

Twenty-two percent by weight of the organic adhesive mixture was added to 78% by weight of silver metal filler. The mixture was stirred under high shear until homogeneous. The resulting paste was then degassed at 1 torr. The paste was dispensed onto silver plated copper lead frames using a starfish dispense nozzle. Bare silicon dice (300×300 mils on a side) were then placed on top and compressed into the adhesive until a 2.0 mil bondline had been attained (this process is virtually instantaneous when using automated "pick and place" equipment. The assembled parts were then cured on a heated surface (hot plate) controlled at 200° C. for two minutes. Additional void test parts (which were assembled in parallel using a 300×300 glass slide to replace the silicon die) showed the cured adhesive film to be free of voiding. Half of the assembled parts were subjected to tensile test immediately. The other half were placed in a pressure cooker at 121° C. for 168 hours (i.e., one week). The pressure cooker is considered to be a very aggressive test that has predictive value for the long term robustness of adhesives used in non-hermetic environments.

Adhesion strength testing was performed on these parts using a "Tinius Olsen 10,000" tensile test machine. Steel cube studs (0.25×0.25×0.8 inches) were attached at room temperature to the top of the die and the bottom of the lead frame using Loctite 415 cyanoacrylate glue. The cubes were attached using a V-block fixturing device to assure their co-linearity. Once the room temperature gluing operation was complete (~one hour later), the entire assembly was loaded into the tensile test machine. Pins were used to secure the steel blocks (through holes present in each of the test blocks) to the upper and lower arms of the stud pull machine. The tensile pull speed used was 3.00 inches per minute, and the adhesion measurement was recorded in terms of pounds of force. The tensile test results for the initial and post pressure cooker parts are presented in Table 1.

TABLE 1

| Initial Adhesion (lbs) | Retained Adhesion (lbs) |
|---|---|
| 191 | 141 |
| 169 | 147 |
| 179 | 112 |
| 180 | 153 |
| 166 | 126 |
| 155 | 138 |
| 174 | 161 |
| 175 | 121 |
| 111 | 133 |
| 149 | 149 |
| 164 | 154 |
| 144 | 119 |

As the results in Table 1 demonstrate, the product was found to have good initial and retained adhesion. The average adhesion for the parts prior to pressure cooker treatment was 163 pounds and after pressure cooker it was 138 pounds. Thus, even after one full week at two atmospheres pressure of steam (14.7 psig, 121° C.) about 85% of the initial adhesion was retained. It is noteworthy that a competitive material which was run at the same time had an initial adhesion of 338 pounds, but dropped down to zero after the pressure cooker treatment.

EXAMPLE 11

A test paste was made that contained one equivalent each of the bismaleimide of Versalink 650 (polytetramethyleneoxide-di-p-aminobenzoate, marketed by Air Products, Allentown, Pa.) and the divinyl ether of tetraethylene glycol. The organic phase had 1% by weight of dicumyl peroxide. Seventy-five percent by weight silver filler was used in the paste. Ten parts were assembled and cured as per the preceding example using this paste that contained no coupling agent. One percent by weight of the same mixed coupling agents noted above were then added to the paste. Another ten parts were assembled and cured using this new paste mix. Both groups of parts were then divided into two sets. Half of the parts from each group were tested for tensile strength immediately and the other half following four hours of immersion in the pressure cooker. Tensile strength measurements were performed according to the procedure described in Example 10. The results of this testing are summarized in Table 2.

TABLE 2

| Tensile Strength of Adhesive Bond | | | |
|---|---|---|---|
| No Coupling Agent | | With Coupling Agent | |
| Initial Value | Post Moisture | Initial Value | Post Moisture |
| 110.7 | 0 | 112.3 | 88.8 |
| 111.2 | 0 | 102.6 | 84.3 |
| 107.7 | 0 | 108.5 | 83.8 |
| 110.5 | 0 | 109.2 | 87.9 |
| 106.5 | 0 | 115.6 | 93.3 |

The data in Table 2 shows that the presence of the coupling agents has a dramatic impact on the survival of the adhesive bond in extreme moisture environments.

EXAMPLE 12

A test was conducted to test the adhesion performance of invention compositions following a one minute cure at 200° C. The bondline used for these parts was also dropped from 2.0 down to 1.0 mils during the attach step. Stress, which is induced by the large thermal mismatch between the silicon and lead frame, increases when the bondline is decreased. The organic adhesive portion of paste consisted of one equivalent each of the BMI prepared according to Example 8, and Vectomer 4010 (i.e., bis(4-vinyloxybutyl) isophthalate). It also contained 4.5% of gamma-methacryloxypropyl-trimethoxysilane coupling agent, as well as 0.95% dicumyl peroxide initiator. A paste was made consisting of 22% by weight of this adhesive composition and 78% by weight of silver flake. The paste was degassed and then used to attach 300×300 mil silicon die to silver plated copper lead frames using the reduced bondline and cure time. Six parts were assembled and cured. Two void test parts (same conditions but using 300×300 mil glass slides to replace the silicon die) were also made. There was no evidence of porosity in the void test parts. Tensile strength measurements were performed according to the procedure described in Example 10. The tensile test values for the other parts were: 116, 114, 119,122, 128 and 134 pounds force.

While the invention has been described in detail with reference to certain preferred embodiments thereof, it will be understood that modifications and variations are within the spirit and scope of that which is described and claimed.

That which is claimed is:

1. An adhesive composition consisting essentially of:
(a) a liquid bismaleimide having the structure:

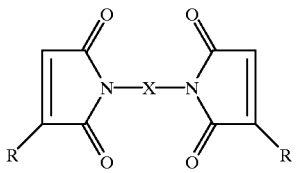

wherein:
each R is independently hydrogen or lower alkyl, and
—X— is:
(1) saturated straight chain alkylene or branched chain alkylene, optionally containing saturated cyclic moieties as substituents on said alkylene chain or as part of the backbone of the alkylene chain, wherein said alkylene species have at least 6 carbon atoms,
(2) aromatic bridging groups having the structure:

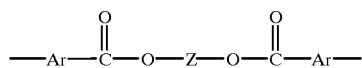

wherein each Ar is a disubstituted or trisubstituted aromatic or heteroaromatic ring having in the range of 3 up to 10 carbon atoms, and Z is:
(i) saturated straight chain alkylene or branched chain alkylene, optionally containing saturated cyclic moieties as substituents on said alkylene chain or as part of the backbone of the alkylene chain, wherein said alkylene species have at least 6 carbon atoms, or
(ii) polyalkylene oxides having the structure:

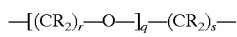

wherein each R is independently as defined above, r falls in the range of 1 up to 10, s falls in the range of 1 up to 10, and q falls in the range of 1 up to 50,
(3) di- or tri-substituted aromatic moieties having the structure:

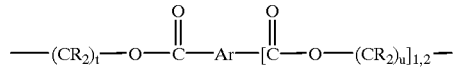

wherein each R is independently as defined above, t falls in the range of 2 up to 10, u falls in the range of 2 up to 10, and Ar is as defined above
(4) polyalkylene oxides having the structure:

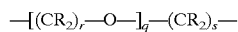

wherein each R is independently as defined above, and wherein each of r, s and q are as defined above, or
(5) mixtures of any two or more thereof,
(b) up to one equivalent of a divinyl compound per equivalent of bismaleimide, wherein said divinyl compound has the structure:

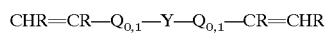

wherein:
each R is independently as defined above,
each Q is independently —O—, —O—C(O)—, —C(O)— or —C(O)O—, and
—Y— is:
(1) saturated straight chain alkylene or branched chain alkylene, optionally containing saturated cyclic moieties as substituents on said alkylene chain or as part of the backbone of the alkylene chain, wherein said alkylene species have at least 6 carbon atoms,
(2) di- or ti-substituted aromatic moieties having the structure:

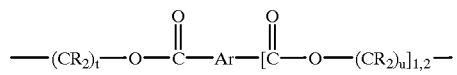

wherein each R is independently as defined above, Ar is as defined above, and each of t and u are as defined above,
(3) polyalkylene oxides having the structure:

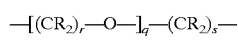

wherein each R is independently as defined above, and wherein each of r, s and q are as defined above, or
(4) mixtures of any two or more thereof,
(c) in the range of 0.1 up to 10 wt % of at least one coupling agent, based on the total weight of the composition, and
(d) in the range of 0.2 up to 3 wt % of at least one peroxide free radical initiator, based on the total weight of the composition.

2. A composition according to claim 1 wherein —Y— is:
—O—[(CH$_2$)$_2$—O—]$_4$—,
—cyclohexyl-C(CH$_3$)$_2$— cyclohexyl —,
—(CH$_2$)$_4$—O—(C$_3$N$_3$)—[O—(CH$_2$)$_4$]$_2$—, wherein —(C$_3$N$_3$)— is a 2,4,6-trisubstituted 1,3,5-triazine,

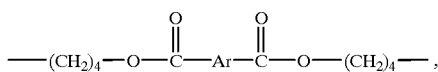

wherein —Ar— is a 1,3-disubstituted phenyl ring, or —Y— is derived from a dimer amine, and includes —(CH$_2$)$_9$—CH(C$_8$H$_{17}$)—CH(C$_8$H$_{17}$)—(CH$_2$)$_9$—.

3. A composition according to claim 1 wherein said coupling agent is a silicate ester, metal acrylate salt, titanate or compound containing a co-polymerizable group and a chelating ligand.

4. A composition according to claim 1 wherein said free radical initiator is a peroxide or an azo compound.

5. A composition according to claim 1 wherein —X— and —Y— are not both aromatic.

6. A composition according to claim 2, wherein said divinyl compound is an acrylate derivative of a dimer amine, wherein Y includes —(CH$_2$)$_9$—CH(C$_8$H$_{17}$)—CH(C$_8$H$_{17}$)—(CH$_2$)$_9$—.

7. An adhesive composition comprising:
(a) a bismaleimide having the structure:

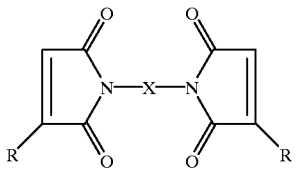

wherein:
each R is independently hydrogen or lower alkyl, and
—X— is derived from a dimer amine, and includes
—(CH$_2$)$_9$—CH(C$_8$H$_{17}$)—CH(C$_8$H$_{17}$)—(CH$_2$)$_9$—
(b) up to one equivalent of a divinyl compound per equivalent of bismaleimide, wherein said divinyl compound has the structure:

CHR=CR—Q$_{0,1}$—Y—Q$_{0,1}$—CR=CHR wherein:
each R is independently as defined above,
each Q is independently —O—, —O—C(O)—, —C(O)— or —C(O)O—, and
—Y— is:
(1) saturated straight chain alkylene or branched chain alkylene, optionally containing saturated cyclic moieties as substituents on said alkylene chain or as part of the backbone of the alkylene chain, wherein said alkylene species have at least 6 carbon atoms,
(2) di- or tri-substituted aromatic moieties having the structure:

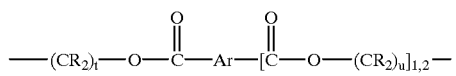

wherein each R is independently as defined above, Ar is as defined above, and each of t and u are as defined above,
(3) polyalkylene oxides having the structure:

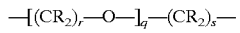

wherein each R is independently as defined above, and wherein each of r, s and q are as defined above, or (4) mixtures of an two or more thereof,
(c) in the range of 0.1 up to 10 wt % of at least one coupling agent, based on the total weight of the composition, and
(d) in the range of 0.2 up to 3 wt % of at least one free radical initiator, based on the total weight of the composition.

8. A die-attach paste comprising:
(I) in the range of about 10 up to about 80 wt % of an adhesive composition comprising:
(a) a bismaleimide having the structure:

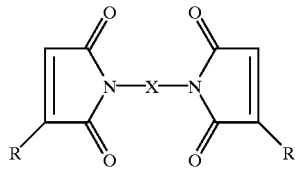

wherein;
each R is independently hydrogen or lower alkyl, and
—X— is:
(1) saturated straight chain alkylene or branched chain alkylene, optionally containing saturated cyclic moieties as substituents on said alkylene chain or as part of the backbone of the alkylene chain, wherein said alkylene species have at least 6 carbon atoms,
(2) aromatic bridging groups having the structure:

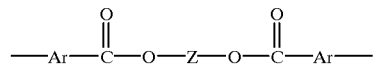

wherein each Ar is a disubstituted or trisubstituted aromatic or heteroaromatic ring having in the range of 3 up to 10 carbon atoms, and Z is:
(i) saturated straight chain alkylene or branched chain alkylene, optionally containing saturated cyclic moieties as substituents on said alkylene chain or as part of the backbone of the alkylene chain, wherein said alkylene species have at least 6 carbon atoms, or
(ii) polyalkylene oxides having the structure:

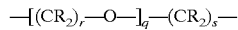

wherein each R is independently as defined above, r falls in the range of 1 up to 10, s falls in the range of 1 up to 10, and q falls in the range of 1 up to 50,
(3) di- or tri-substituted aromatic moieties having the structure:

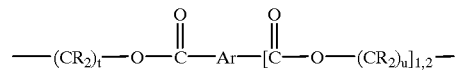

wherein each R is independently as defined above, t falls in the range of 2 up to 10, u falls in the range of 2 up to 10, and Ar is as defined above
(4) polyalkylene oxides having the structure:

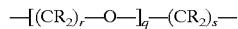

wherein each R is independently as defined above, and wherein each of r, s and q are at defined above, or (5) mixtures of any two or more thereof,
(b) up to one equivalent of a divinyl compound per equivalent of bismaleimide, wherein said divinyl compound has the structure:

$$CHR=CR-Q_{0,1}-Y-Q_{0,1}-CR=CHR$$

wherein:
each R is independently as defined above,
each Q is independently —O—, —O—C(O)—, —C(O)— or —C(O)O—, and
—Y— is:
(1) saturated straight chain alkylene or branched chain alkylene, optionally containing saturated cyclic moieties as substituents on said alkylene chain or as part of the backbone of the alkylene chain, wherein said alkylene species have at least 6 carbon atoms,
(2) di- or tri-substituted aromatic moieties having the structure:

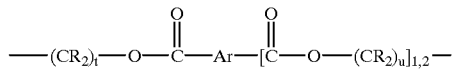

wherein each R is independently as defined above, Ar is as defined above, and each of t and u are as defined above,
(3) polyalkylene oxides having the structure:

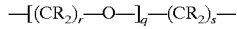

wherein each R is independently as defined above, and wherein each of r, s and q are as defined above, or (4) mixtures of any two or more thereof,
(c) in the range of 0.1 up to 10 wt % of at least one coupling agent, based on the total weight of the composition, and
(d) in the range of 0.2 up to 3 wt % of at least one free radical initiator, based on the total weight of the composition; and
(II) in the range of about 20 up to 90 wt % of a conductive filler.

9. A composition according to claim 7, wherein —Y— is:
—O—[(CH$_2$)$_2$—O—]$_4$—,
-cyclohexyl-C(CH$_3$)$_2$-cyclohexyl
—(CH$_2$)$_4$—O—(C$_3$N$_3$)—[O—(CH$_2$)$_4$]$_2$—, wherein —(C$_3$N$_3$)— is a 2,4,6-trisubstituted 1,3,5-triazine,

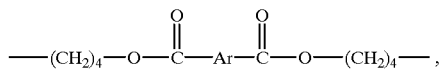

wherein —Ar— is a 1,3-disubstituted phenyl ring, or —Y— is derived from a dimer amine, and includes —(CH$_2$)$_9$—CH(C$_8$H$_{17}$)—CH(C$_8$H$_{17}$)—(CH$_2$)$_9$—.

10. A composition according to claim 7, wherein said coupling agent is a silicate ester, metal acrylate salt, titanate or compound containing a co-polymerizable group and a chelating ligand.

11. A composition according to claim 7, wherein said free radical initiator is a peroxide.

12. A composition according to claim 8, wherein said conductive filler is electrically conductive.

13. A composition according to claim 8, wherein said conductive filler is thermally conductive.

* * * * *